United States Patent [19]

Brahme

[11] Patent Number: 4,672,212
[45] Date of Patent: Jun. 9, 1987

[54] MULTI LEAF COLLIMATOR

[75] Inventor: Anders Brahme, Bromma, Sweden

[73] Assignee: Instrument AB Scanditronax, Uppsall, Sweden

[21] Appl. No.: 706,771

[22] Filed: Feb. 28, 1985

[51] Int. Cl.[4] .............................................. G21K 1/04
[52] U.S. Cl. .................................. 250/505.1; 378/150; 378/153
[58] Field of Search ............... 250/505.1, 515.1, 497.1, 250/498.1, 492.1; 378/150, 151, 152, 153, 206, 147

[56] References Cited

U.S. PATENT DOCUMENTS

| | | | |
|---|---|---|---|
| 2,904,692 | 9/1959 | Gscheidlen | 378/152 |
| 4,169,228 | 9/1979 | Briska et al. | 250/272 |
| 4,432,370 | 2/1984 | Hughes et al. | 128/654 |
| 4,463,266 | 7/1984 | Brahme | 250/505.1 |

FOREIGN PATENT DOCUMENTS

| | | | |
|---|---|---|---|
| 192300 | 11/1907 | Fed. Rep. of Germany | 378/150 |
| 3030332 | 2/1982 | Fed. Rep. of Germany | 378/151 |
| 2500677 | 8/1981 | France | 250/505.1 |

*Primary Examiner*—Bruce C. Anderson
*Assistant Examiner*—Paul A. Guss
*Attorney, Agent, or Firm*—Lewis H. Eslinger

[57] ABSTRACT

A multi leaf collimator for a radiation beam the particles of which is selected from the group consisting of high energy photons, electrons, protons and heavy ions which are emitted from a small effective radiation source. The collimator comprises low hight, elongated, curved, in cross section wedge-shaped leaves arranged side by side in opposed pairs. The configuration is such that the parts of the surfaces intersecting the irradation field will always be directed generally towards the radiation source. A protective casing surrounding a frame on which the collimator is mounted can be filled with helium gas to optimize the collimator for use with electron and photon beams in the energy range from 1 up to 50 MeV. The individual settings of the leaves are supervised by a TV-camera which also can be used to set the leaves in predetermined positions.

12 Claims, 8 Drawing Figures

MULTI LEAF COLLIMATOR

CROSS REFERENCES TO RELATED PATENTS AND PATENT APPLICATIONS

U.S. Pat. No. 4,463,266 to A. Brahme entitled "Neutron Collimator" issued July 31, 1984 and assigned to the same assignee as the present invention.

BACKGROUND OF THE INVENTION

This invention pertains to a multi leaf collimator for a beam of radiation the particles of which are selected from the group comprising high energy photons, electrons, protons and heavy ions to the extent not already covered by said U.S. Pat. No. 4,463,266.

Modern beam radiation technique makes use of high energy particles to irradiate deep seated tumours. High energy photons and electrons with energies in the order of 1 to 50 MeV are considered for radiation therapy.

In the neutron collimator described in said patent wedge-shaped slabs are arranged in opposed pairs such that the inner opposed edges of each pair of slabs are always directed towards the effective radiation source. This will prevent the formation of an undesired penumbra, that is a half shaded area extending in the longitudinal direction of motion behind each slab. Due to the wedge like shape of each slab also the plane main side surfaces of each slab will be directed towards the radiation source thereby also preventing the formation of an undesired penumbra in the direction perpendicular to the said longitudinal direction.

If high energy particles of the kind referred to above should be used the slabs of said neutron collimator are much to thick to absorb the particles and will generate undesirable scatter. Since the slabs are of solid tungsten and low carbon soft iron the known neutron collimator is heavy and requires a sturdy frame for supporting the slabs. This is a drawback from constructional point of view.

Moreover, if high energy particles of the kind referred to above in particular electrons are to be used in a collimator the air molecules within the collimator will interact with the particles of the radiation beam thereby giving rise to an effect appearing as if the effective radiation source is no longer, as desired, a point but rather an area of a certain extension. This is undesired since the particles emitted from the periphery of said area will cause an undesired scatter on the inner opposed edges and an increased penumbra resulting from the fact that neither the said inner edges nor the plane main side surfaces of the slab will point to the effective radiation source.

Should the known collimator be used for treatment with high energy photons said photons will collide with the atoms of the air giving rise to Compton interactions and secondary electrons, which will give rise to a substantial, non-desired increase of the dose to the skin of the patient.

SUMMARY OF THE INVENTION

The present invention concerns a multi leaf collimator avoiding the drawbacks of the neutron collimator in accordance with the prior art in order to produce high quality variable field shapes and to maintain a point type radiation source particularly when high energy electrons and photons are used for radiation therapy. Moreover, the weight of the collimator will be reduced.

In one aspect of the present invention there is the provision of a multi leaf collimator for a beam of radiation the particles of which ar selected from the group comprising high energy photons, electrons, protons and heavy ions which are emitted from a point type effective radiation source, comprising a protective radiation casing, a frame surrounded by the casing, a plurality of pairs of opposed, elongated, curved in cross section wedge-shaped leaves, wherein adjacent leaves are placed side by side such that a fan-shaped configuration converging towards an apex at the effective radiation source is achieved, each wedge-shaped leaf being mounted for a combined rotational and translational movement on a support structure such that the leaves of each pair are mounted for motion towards and away from each other along a path which intersects the edge of the radiation field from the radiation source at right angle, the inner edge surface as well as the main surfaces of each leaf always being directed generally towards the radiation source setting means for setting each leaf in a predetermined position along each individual path and read out means to determine the position of the leaves.

In another aspect of the invention the protective casing is filled with helium gas at atmospheric pressure.

DESCRIPTION OF THE PREFERRED EMBODIMENT

Figure 1:
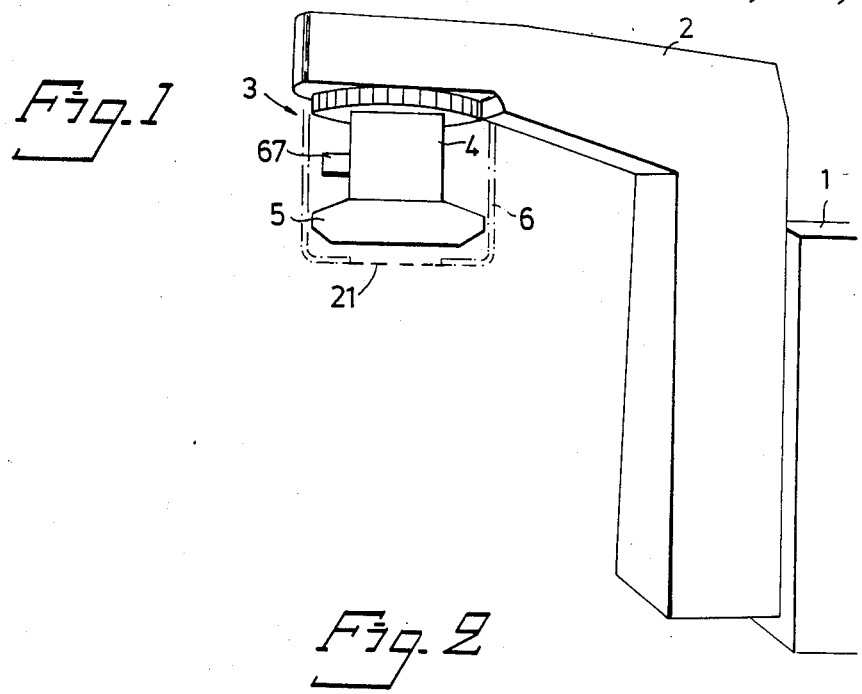
FIG. 1 is a perspective view of a radiation therapy gantry wherein the multi leaf collimator of the present invention is used.

In FIG. 1 there is schematically shown an accelerator 1 for the production of a beam of high energy electrons which by a beam transportation system and a beam optical system within a rotary gantry 2 is directed into a rotary radiation head 3 mounted at the end of the gantry 2. The radiation head 3, comprises a frame 4, a multi leaf collimator 5 in accordance with the present invention and a protective casing 6 shown in broken lines. Further to the multi leaf collimator 5 a conventional block collimator 7 is provided on the frame 4 to collimate the radiation beam in a direction perpendicular to the longitudinal direction of motion of the leaves of the collimator 5 in accordance with the present invention.

Figure 2:
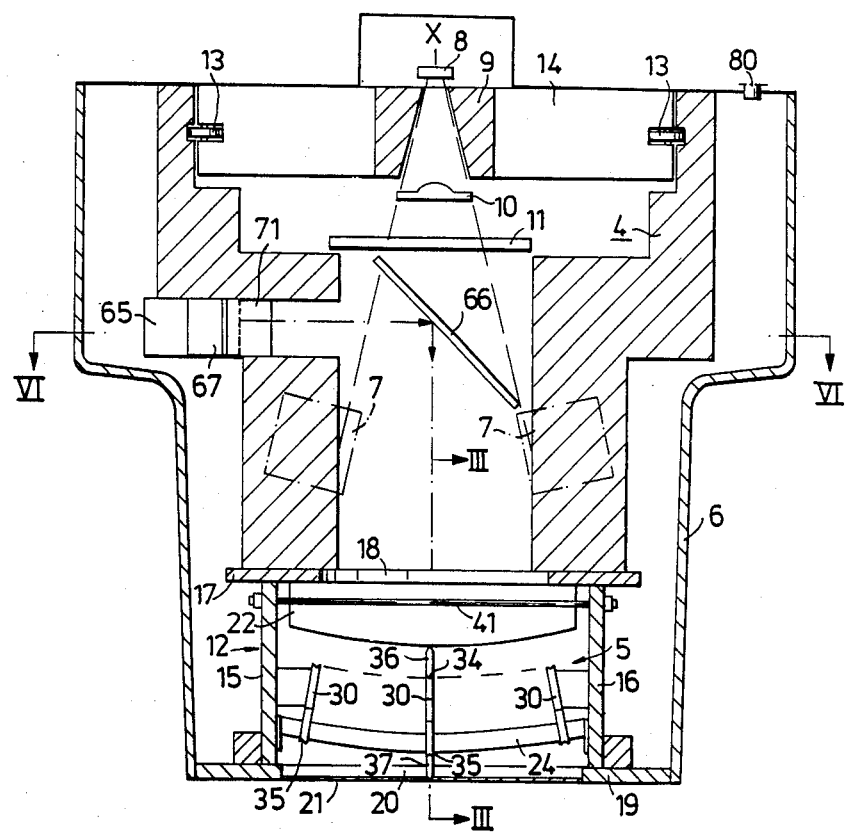
FIG. 2 is a sectional view of the radiation head shown in FIG. 1 provided with a collimator in accordance with the present invention, wherein the radiation head is seen from the side and some parts have been omitted for clarity.

As appears from FIG. 2 the accelerated electron beam is projected onto a target 8. Depending on the material of the target and the particles of the incoming beam the target will act as a source of high energy photons, protons, electrons or heavy ions. This is well-known to the man skilled in the art and will therefore not be described further. Positioned downstream from the target 8 there is a heavy metal primary collimator 9 which is used to limit the maximum desired radiation beam. Positioned downstream of the primary collimator 9 and aligned with the opening of the collimator 9 there may be a flattening filter 10 and an ionization chamber 11. The ionization chamber 11 is provided in the radiation field to measure dose rate and for other beam controlling purposes known per se and therefore not described here. Further downstream the block collimator 7 is positioned. Still further downstream the multi leaf collimator 5 in accordance with the present invention is positioned. The multi leaf collimator is mounted in a support structure generally designated 12. The support structure 12 is mounted at the bottom of the frame 4. The frame 4 and the elements mounted thereon are rotably supported by a bearing 13 on a circular top mounting plate 14.

The support structure 12 comprises two opposed rectangular side walls 15 and 16 mounted at their respective upper end to a rectangular base plate 17 having a central opening 18 therein for the unhindered passage of the radiation. The side walls are at their lower end mounted to a lower plate 19 also provided with a rectangular opening 20 which is covered by a thin transparent film 21 forming the front surface of the radiation head 3 Between the side walls 15 and 16 opposite pairs of upper and opposite pairs of lower curved support bars 22, 23 and 24, 25 respectively are extending. (Compare FIG. 3)

Figure 3:
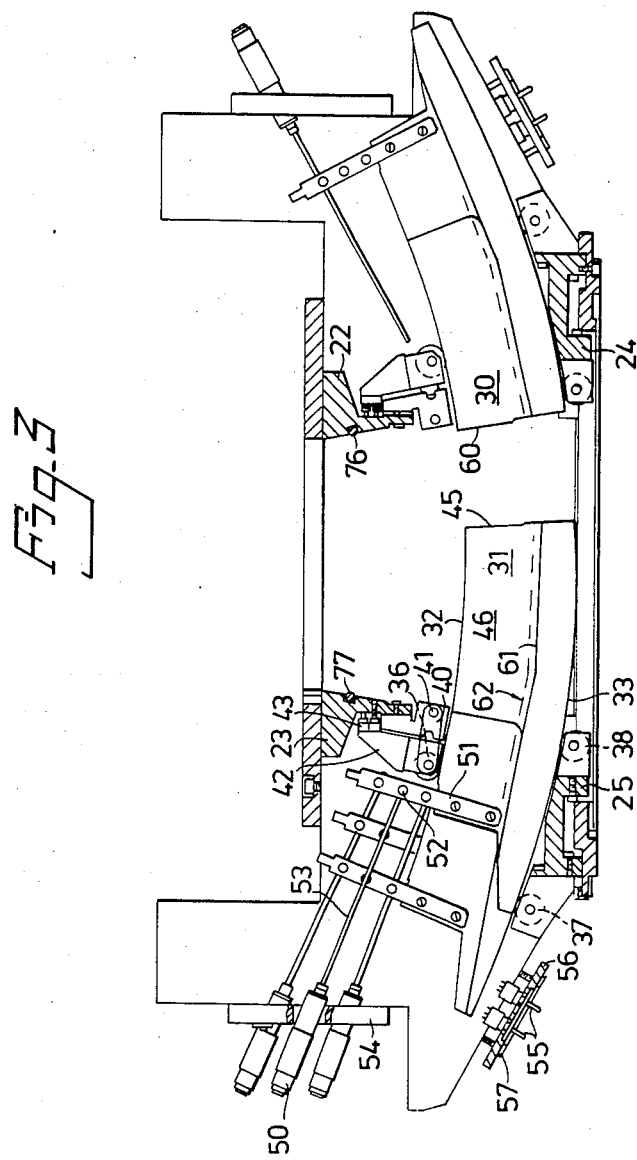
FIG. 3 is a sectional view of the collimator along lines III—III in FIG. 2.
Figure 4:
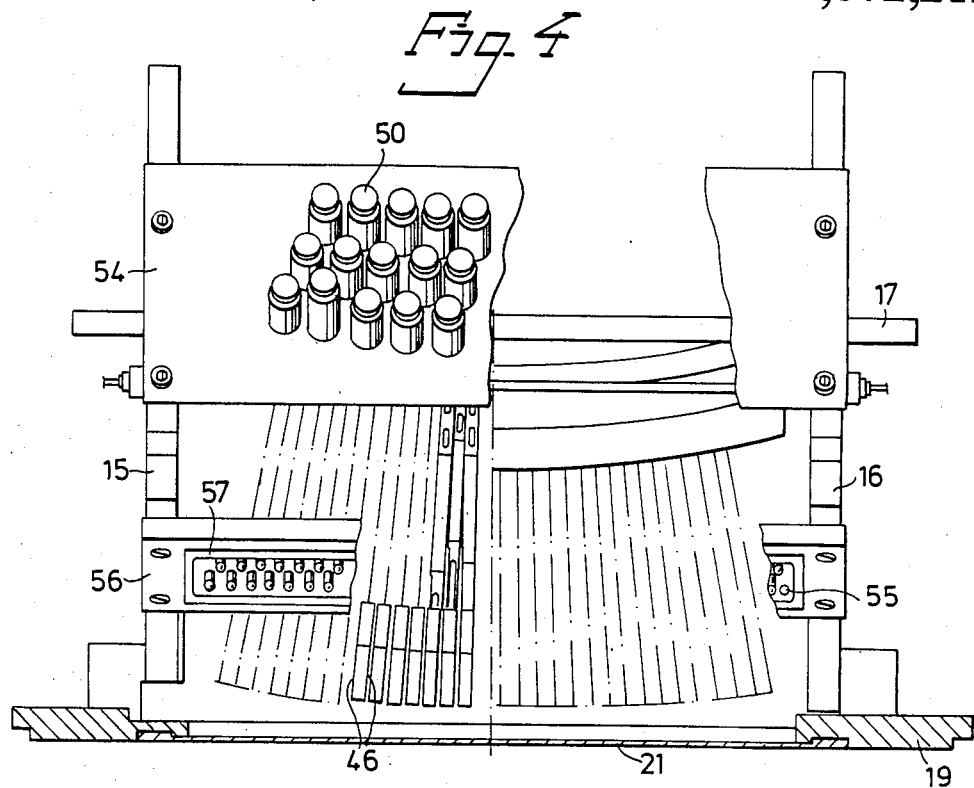
FIG. 4 is a side view similar to that of FIG. 2 showing additional components of the collimator in accordance with the invention and omitted in FIG. 2 for clarity reasons.

A number of opposite pairs of elongated, curved and in cross section tapering leaves 30, 31 are slidably mounted between the upper and lower support bars 22-25. Since each leaf of each pair is supported in the same manner only leaf 31 and its support structure will be described in detail. It should therefore be understood that the corresponding constructional parts are provided for a leaf 30. Moreover, this construction is repeated for each further leaf 31 and each further leaf 30. In the preferred embodiment there are 32 pair of leaves 30, 31. Each leaf is made by solid lead, tungsten, uranium or by another material having a high density and atomic number or more generally high interaction cross section for the radiation at hand. The height of each leaf is about 70 mm and the length about 30 cm. As seen from FIG. 4 each leaf is in cross section tapering and the width of the leaf is of the order of about 7 mm. Each leaf has a curved upper and a curved lower surface 32 and 33 respectively. The curvature is such that each surface would form a part of an imagined circle having its center close to the effective source of radiation which in FIG. 2 is marked with an X. In the upper surface 32 there is a longitudinal V-shaped slot 34 schematically shown in FIG. 2 and a corresponding V-shaped slot 35 is provided in the lower surface 33. An upper roller 36 is spring biased into engagement with the upper slot 34. Two lower rollers 37 and 38 are supporting the leaf 32 in its lower slot 35. Each roller 37, 38 is rotary supported by the lower support bar 25 while the upper roller 36 is supported by the upper support bar 23 by a lever 40 at one end pivoting around a pivot shaft 41 common to all pair of leaves and at the other end thereof rotably mounting roller 36. An L-shaped plate 42 is at one end thereof rotably attached to a lever 40 and is at its opposite end attached to a compression spring 43 mounted at support bar 23. The provision of the compression spring 43 pressing roller 36 into engagement with the upper slot of the leaf 32 will provide for a smooth running of the leaf along a curved, circular path between the extreme positions of each leaf. In FIG. 3 leaf 31 is shown in its extreme projected position while leaf 30 is shown in its extreme retracted position. On moving the leaf 31 between the three rollers the leaf will perform a translational as well as rotational motion.

The inner edge surface 45 of leaf 31 is arranged so as to always be in alignment with the effective radiation source X, that is said edge surface 45 forms a part of a radius of an imagined circle having its center in X. It is thus apparent that the radiation beam emitted from the effective radiation source X will sweep parallel along the inner edge surface 45 leaving no undesired penumbra. Should the edge 45 form an angle to said imagined radius then an undesired penumbra would result. In order to avoid such undesired penumbra also in a direction perpendicular to the longitudinal direction, i.e. the direction of motion, of leaf 31, that is in a direction generally perpendicular to the plane of the FIG. 2 drawing, the two main surfaces, of which one is shown at reference numeral 46, of leaf 31 are tapering so as to always point in the direction of the effective radiation source X. Accordingly the leaves 31 when mounted in the shown side by side relationship will form a fan-like configuration shown in FIG. 4 with the apex of the fan at X. Accordingly, a double alignment of the parts of the collimator which intersect the radiation field is achieved. In the above-mentioned US Patent this double alignment is termed double focusing.

Setting means in order to set the position of each leaf is provided in the form of a motor 50 and an upwardly directed extension 51 provided on each leaf 31. The extension may be in the form of a bar which at its lower end is secured by screws to leaf 31 and which at its upper end is provided with a number of through openings. For leaf 31 a pivot pin 52 is provided in the middle opening, said pivot pin being provided with a through hole having an internal thread. A threaded output shaft 53 of the motor 50 is screwed into the threaded through hole of the pivot pin and it is thus apparent that rotation of the output shaft will cause leaf 31 to move along said curved circular path. Since the thickness of the leaves 30, 31 are less than the diameter of the motors the motors of contiguous leaves 31 are arranged in rows and are slightly displaced relative each other in the manner indicated in FIG. 4. Each step motor 50 is pivotably mounted in a through opening provided in a motor mounting bar 54 extending between the side walls 15, 16. Each motor is individually controllable by way of a switch 55 provided on a switch mounting bar 56 also extending between said side walls 15, 16. A gasket 57 surrounds the switches 55 on the switch mounting bar and forms a gas tight seal against the protective casing 6 which at the area of the switch mounting bar is provided with a through opening so that each motor can be manually controlled by operating the switch.

Figure 5:
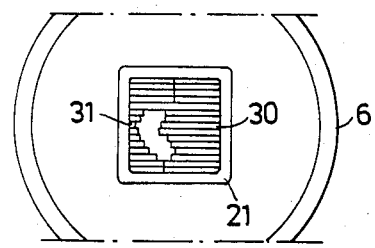
FIG. 5 is a bottom view of the beam radiation head of FIG. 1 as seen from below.

As can be seen from FIG. 3 the inner edge 45 is provided with a step. A complementary step is provided in the opposite inner edge 60 of leaf 30 so that when the leaves are brought into contact with each other such as is the case with the upper and lower leaves shown in FIG. 5 no radiation will penetrate the joint between the contacting edges. In a similar manner and for the same purpose the main surface 46 is provided with a step, generally shown at 61, and a complementary step is provided in the opposite main side surface of the leaf 31 as is shown by the broken line 62.

As appears from FIG. 2 a bulb 65 is provided at the outside of frame 4. The light from the bulb is transmitted through a semi-transparent mirror 71 and is reflected by a mirror 66 downstream from the radiation head. The arrangement is such, that the light from the bulb will illuminate the irradiated surface (for example the body of a patient). The illuminated surface would then be the radition field as set by the multi leaf collimator 5, for example the off center kidney-shaped radiation field shown in FIG. 5.

In order to reduce the interaction of the radiation beam with the molecules of the air the air within the protective casing 6 is replaced with helium gas which is introduced through a valve 80 and is held at atmospheric pressure within the casing.

Figure 6:
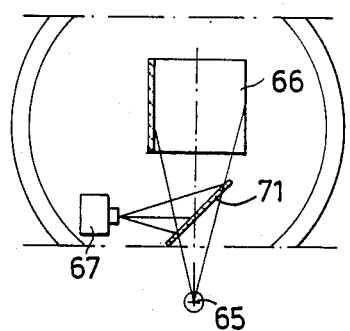
FIG. 6 is a section view along VI—VI in FIG. 2.
Figure 7:
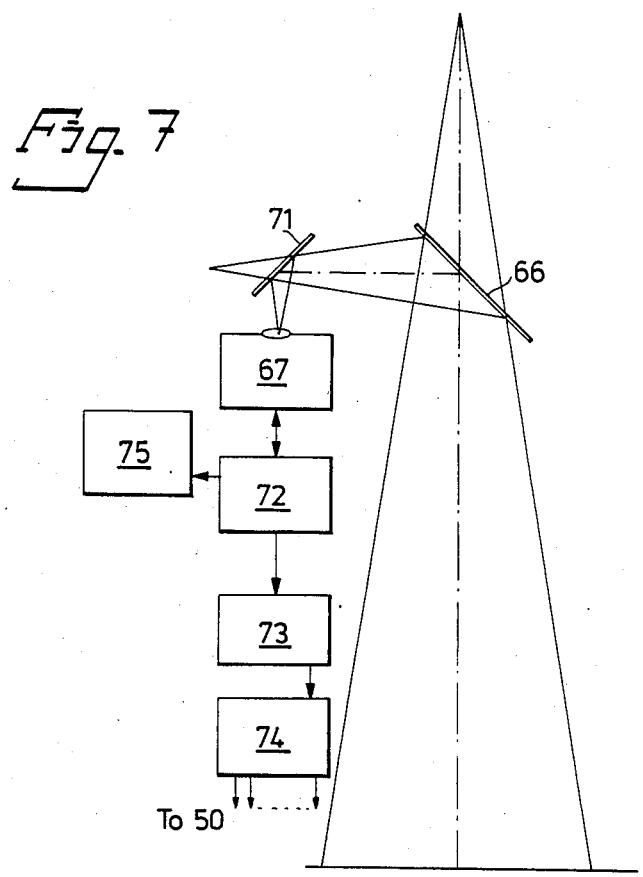
FIG. 7 is a block diagram showing the leaf collimator read out and control system.

Prior to the present invention the position of every leaf 31, 32 was supervised by the personal. The position of each leaf was indicated on a meter which by two conductors was connected to a sliding contact of a potentiometer and the fixed contact of the same potentiometer. The sliding contact in turn was moved by the output shaft of the motor thereby indicating the actual position of a collimator blade in the form of a voltage reading on the meter. For 64 slabs of the kind used in said U.S. patent this supervision system thus required at least 68 conductors to be drawn from the radiation head. Now, in accordance with the present invention said conductors are replaced by one single coaxial cable connected to a television camera 67 forming part of a read out and control system by which each individual leaf is set in a predetermined position along each individual path previously described. The read out system is shown in detail in FIGS. 6 and 7 and comprises further to said TV-camera a mirror system including the semi-reflector mirror 66 and a semi-reflective mirror 71. The leaf collimator control system also includes a TV-camera control unit 72 a data processor 73 and a motor drive unit 74 including a separate drive units for each individual motor 50 and a TV-monitor 75.

The TV-camera is so positioned as it through the mirrors appears to be at the centre X of the beam. It will thus, "look" into the radiation head and see the leaf collimator 5 from the effective radiation source. Ambient light reflected from the surface to be radiated is directed upstream the radiation head and will be seen by the television camera after reflection in mirrors 66 and 71. Replacing mirror 71 with a transmission filter may further improve the contrast of the television picture. Suppose the transmission filter is bluish, then the bluish portion of the light from the bulb 65 is filtered out and yellow like light will illuminate the blade collimator from above. Ambient light reflected from the radiated surface will, however, contain the bluish component just filtered out from the light which illuminates the collimator from above and accordingly the overall contrast is improved. Alternatively the read out is performed with the field light from the bulb 65 on. The upper surface of the leaves is then provided with a reflective surface reflecting the field light back into the TV-camera.

Figure 8:
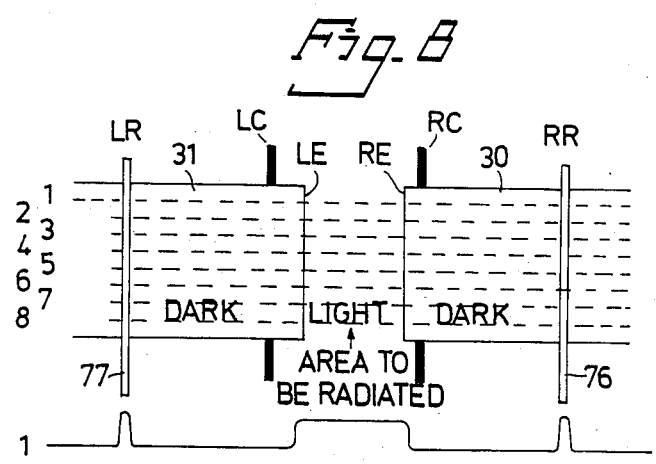
FIG. 8 is an enlarged view of a pair of opposite leaves as seen by a television camera incorporated in the leaf collimator read out system.

The TV-camera 67 is scanning the leaves along a direction which is parallel to the path along which each leave is movable. Each scanning line is accordingly scanning a pair of two opposing leaves as is illustrated in FIG. 8. In the preferred embodiment each leaf is scanned by eight lines 1–8 and the position of each leaf is determined by the light/dark transition appears in each scanning line. The TV-camera control unit 72 includes an A-D converter for conversion of the analog picture information contained in each scanning line into data position signals which are processed by the processor 73. As is apparent from FIG. 8 each scanning line comprises information on the position of the right end of the left leaf 31 indicated by LE in the drawing and the position of the left end of the right leaf 30 indicated by RE. For each set of leaves 30, 31 there is a reference mark formed by light bars 76 and 77 respectively. Each light bar comprises a rod of polymethyl/methacrylate (PMMA) which at one end surface thereof is provided with a bulb directing its light into the rod. In FIG. 8 light bar 76 is indicated by RR (right reference) and light bar 77 by LR (left reference). In the preferred embodiment of the invention data relating to the positions of the contour line of the field to be radiated is stored in the processor and are compared with the data position signals relating to LE and LR. In FIG. 8 LC represents a portion of the left contour line of the field to be radiated while RC represents a portion along the right hand of said contour line. Accordingly, the radiation field should be the area between LC and RC in FIG. 8. In FIG. 8 it is also apparent that LE of leaf 31 should be moved to the left into alignment with LC in order to take the correct setting. Similarly LR of leaf 30 should be moved to the right into alignment with RC. In the processor 73 data representing the current position of LE are continiously compared with data representing the position of LC and if there is any deviation therebetween the processor is programmed to output a control signal to the motor 50 so as to energize the latter until it has moved LE of 31 into alignment with LC. In a similar way the motor 50 driving leaf 30 is controlled by the processor.

Although theoretically it would be possible to obtain the necessary position data for each pair of opposing leaves by scanning each pair just once it is preferred to obtain each required datum, i.e. LR, LE, RE and RR in separate scannings. As noted previously a pair of opposing leaves is scanned in eight lines 1–8 as shown in FIG. 8. In line 1 the datum representing the position of LR is taken. During scanning line 2 no data are taken, during scanning line 3 LE is taken, during 4 no date are taken, during line 5 RE is taken, during line 6 no data are taken, during line 7 RR is taken and during line 8 no data are taken.

The position of the blades of the collimator can be viewed in the TV-monitor 75 also forming part of the read out system.

In the embodiment described above the positions of LC and RC are stored in the processor 72 at a time prior to the actual setting of the leaves 30, 31. LC and RC position data may be entered manually into the processor or may be taken directly from the central processor of a computerized tomography system. In accordance with a further embodiment of the invention the contour line of the field to be irradiated is drawn directly on the patient's skin and data relating to the contour line as drawn are taken for example during scanning line 2 for LC and during scanning line 4 for RC.

Having thus described the invention, I claim:

1. A collimator for a beam of radiation the particles of which are selected from the group comprising high energy photons, electrons, protons, and heavy ions, which are emitted from a point type effective radiation source, comprising a protective radiation casing filled with helium gas, a frame surrounded by the casing, a plurality of pairs of opposed, elongated, curved, in cross section wedge-shaped leaves, wherein adjacent leaves are arranged side by side such that a fan-shaped configuration converging towards an apex at the effective radiation source is achieved, each wedge-shaped leaf being mounted for a combined rotational and translational movement on a support structure such that the leaves of each pair are mounted for motion towards and away from each other along a path which intersects the edge of the radiation field from the radiation source at a right angle, the inner edge surface as well as the two main surfaces of each leaf always being directed generally towards the radiation source, setting means for setting each leaf in a predetermined position along each individual path, bearing means provided between each leaf and the support structure, and read out means are provided to determine the position of the leaves by optical inspection of the leaves from a point that corresponds to the center of said radiation source.

2. A collimator in accordance with claim 1 wherein said helium gas is held at atmospheric or lower pressure.

3. A collimator in accordance with claim 1 wherein said leaves are made of a material having a high density and high atomic number, such as lead, tungsten and uranium.

4. A collimator in accordance with claim 3 wherein said setting means comprise individual motor means for setting the position of each leaf.

5. A collimator in accordance with claim 1 where in said read out means comprises TV-camera means, mirror means for viewing the radiation field from a point which corresponds to the centre of the radiation source on which the leaf collimator is focussed, the optical center of said TV-camera means being located in said point, motor means for each respective collimator leaf to set the position of said leaf, a TV-camera read out device comprising AD converting means for converting the TV-picture information into data position signals representing the position of each individual leaf, a data processor for receiving said data signals and comparing said signals with data position signals which represent the desired configuration of the radiation field and for generating, should there be any deviation between the compared data position signals, a signal to each motor in order to move the leaf to its desired position.

6. A collimator in accordance with claim 5, characterized in that said TV-camera means is arranged to establish the position of each collimator leaf by detecting light/dark transitions in predetermined lines of the TV-camera picture.

7. A collimator in accordance with claim 6, characterized in that the position of each collimator leaf is determined by the light/dark transition at a front surface of each collimator leaf with reference to stationary light bar means mounted in the collimator.

8. A collimator in accordance with claim 7, characterized in that each leaf is scanned by several TV-picture lines extending parallel to the top surface of each collimator leaf and that the light/dark transition in at least each second line is used to obtain the following data relating to the position of a leaf:

(1) the actual position of said front surface of a leaf and (2) a reference position as established by said light bar means.

9. A collimator in accordance with claim 7, characterized in that data relating to the contour line of the radiation field configuration are stored, prior to the setting of the collimator leaves, in the memory of said data processor.

10. A collimator in accordance with claim 9, characterized in that data relating to the position of the radiation field are taken by the TV-camera means from a contour line drawn directly on the surface of the object to be radiated by sensing the light/dark transition of said contour line.

11. A collimator in accordance with claim 1 characterized in that the position of each collimator leaf is determined by the light/dark transition at a front surface of each collimator leaf with reference to a reflector means mounted in the collimator.

12. A collimator in accordance with claim 1, wherein said bearing means comprises for each slab; a pair of lower rollers supporting the respective slab at its lower surface and an upper roller spring biased into engagement with the upper surface of said slab.

* * * * *